United States Patent [19]

Mizus

[11] Patent Number: 4,960,122
[45] Date of Patent: Oct. 2, 1990

[54] ENDOTRACHEAL TUBE REPLACEMENT OBTURATOR

[76] Inventor: Irving Mizus, 4308 47th St. NW., Washington, D.C. 20016

[21] Appl. No.: 190,974

[22] Filed: May 6, 1988

[51] Int. Cl.⁵ .......................................... A61M 16/00
[52] U.S. Cl. ........................... 128/207.14; 128/200.26
[58] Field of Search ...................... 128/200.26, 207.14, 128/207.15, 207.17

[56] References Cited

U.S. PATENT DOCUMENTS

| | | | |
|---|---|---|---|
| 4,244,362 | 1/1981 | Anderson | 128/200.26 |
| 4,444,185 | 4/1984 | Shugar | 128/200.26 |
| 4,449,522 | 5/1984 | Baum | 128/200.26 |
| 4,527,559 | 7/1985 | Roxburg et al. | 128/207.17 |

OTHER PUBLICATIONS

"Self-Lubricated Stylet for Endotracheal Tubes", 4/68, by John Marshall, M.D., Journal of the American Society of Anesthesiologists, Inc., vol. 29, #2, p. 385.

*Primary Examiner*—Edgar S. Burr
*Assistant Examiner*—Aaron J. Lewis
*Attorney, Agent, or Firm*—Sughrue, Mion, Zinn, Macpeak & Seas

[57] ABSTRACT

A system for replacing a tracheal tube uses an obturator that is inserted into the existing tube until it protrudes out from the distal end. The old tube is then slid out using the obturator as a guide. A new tube is inserted along the obturator until it has been properly inserted. The obturator is then removed. The obtuator has a flexible atraumatic tip at one end and a gripping section at the outer end. It is made from a flexible radiopaque material and has positioning marks to facilitate use with both endotracheal and tracheostomy tubes.

5 Claims, 1 Drawing Sheet

ENDOTRACHEAL TUBE REPLACEMENT OBTURATOR

FIELD OF THE INVENTION

This invention relates to a medical instrument and the use thereof and in particular, a technique by which replacement of an endotracheal or a tracheostomy tube may be accomplished in a fast and safe manner.

BACKGROUND OF THE INVENTION

In the practice of pulmonary and critical care medicine it is common to use either an endotracheal tube or a tracheostomy tube to maintain control over the air passages Such devices are well known and generally comprise a tube, having an inside diameter in the range of 7mm-9mm for an adult, which is positioned in the trachea to ensure that adequate ventilation and oxygenation is maintained in a safe and stable manner. The proximal end of endotracheal and tracheostomy tubes has a fitting so that the tube can be connected to a respirator or other source of air -oxygen mixture. The lower or distal end has an inflatable annular cuff to seal the tracheal zone with the exception of the endotracheal tube.

The replacement of either an endotracheal tube or a tracheostomy tube has been performed in the past by withdrawing the old tube and then through either the nose or mouth in the case of the endotracheal tube or via an incision in the neck in the case of a tracheostomy tube, placing a new tube into the trachea. This procedure is complicated, time consuming and incurs a degree of risk to the patient. It is time consuming in that the replacement essentially comprises the removal of an old tube and the insertion of a new one as though no guide or preplacement had existed. Each replacement then, is essentially a procedure which starts without any guide or indication of proper insertion location distance or the like. Moreover, during the period between removal of the old tube and insertion of the new tube, access to the tracheal area can constrict or may have already become so edematous that insertion of the new tube may be difficult or impossible because of inadequate anatomic definition.

The method of reintubation may expose the patient to risks of bleeding, trauma, airway perforation, or needless exposure to medicines which may add potential complications to the procedure, mistaken esophageal intubation, or at times hazardous positioning of the head or neck. These inherent risks would potentially expose the patient to inadequate ventilation, oxyqenation and/or airway control during this period of loss of function and the presence of the endotracheal tube.

As can be appreciated, in a situation where a patient requires an endotracheal tube to assist in a patient's life support system any delay may present potentially serious complications and/or death. In addition tracheal tube replacement is therefore considered a procedure carrying a degree of associated risk whose completion requires highly trained practitioners.

SUMMARY OF THE INVENTION

Given these deficiencies in state of the prior art techniques and equipment, it is an object of this invention to provide a system for replacement of a tracheal tube in an already intubated patient, that may be accomplished in a safer and more expedient manner.

It is a further object of this invention to provide a device which reduces the risks of bleeding, trauma, airway perforation, exposure to medicines, hazardous head and neck positioning while eliminating the risk of esophageal intubation or control of airway access.

This invention thereby provides for easier, faster and safer replacement of an endotracheal tube or a tracheostomy tube while maintaining control of the air passages at all times.

A further object of this invention is to provide a method of replacement of an endotracheal or tracheostomy tube.

These and other objects of this invention are accomplished by employing an obturator which is used in conjunction with the existing tracheal tube for purposes of positioning and guiding removal of both the old tube and insertion of a new tube. In accordance with this invention, once it has been decided that an already endotracheally intubated patient is medically indicated to have their endotracheal tube replaced with a new tube, (prior to extubating the patient) a replacement obturator, in accordance with this invention, is advanced into the trachea through the existing endotracheal tube already in place. The obturator is inserted until a positioning mark is aligned at the connection end of the endotracheal tube.

The distal end inserted first has a tapered soft atraumatic tip design. The opposite end has a knurled, grooved, or handle portion to allow for positive gripping. The obturator itself is comprised of a flexible elastomer or plastic material with a flexible metal core or, a composite elastomer having the necessary flexibility but inherent rigidity to be maintained during the procedure. The material is radiopaque.

With the obturator in place, the inflated cuff on the endotracheal tube is deflated and the tube is removed by sliding it over the obturator out of the trachea and discarded. The obturator remains in place. Next, a new endotracheal tube is slid over the obturator and aligned with the connection end at the positioning mark. Finally, the obturator is removed leaving the new endotracheal tube in place. The tracheal cuff is inflated and its position is verified in a routine manner.

In the case of tracheostomy tubes, the procedure is the same except that the obturator has a different replacement position mark given the shallow location of the connection port vis-a-vis the distal trachea.

This invention will be described in greater detail by referring to the attached drawings and the description of the preferred embodiment that follows.

DESCRIPTION OF THE PREFERRED EMBODIMENT

Referring now to FIGS. 1-4, the apparatus and method in accordance with this invention will be described. FIGS. 1-4 provide a view of the use of this invention for endotracheal tube exchange. It will be appreciated by one of skill in this technology that this same technique can be applied for tracheostomy tube replacement, the only difference being the sites of entry and exit. In the context of a tracheotomy tube, egress into the trachea is through an incision in the neck as opposed to utilizing the mouth or nasal passages. It will also be appreciated that the technique is applicable for entry utilizing nasal passages.

Figure 1:
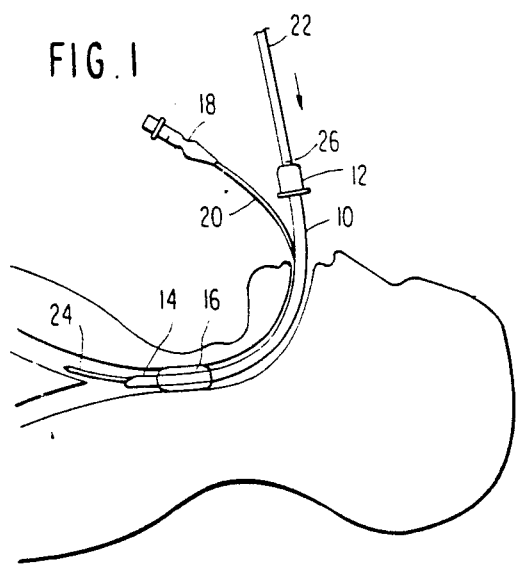
FIGS. 1-4 are schematic illustrations delineating the steps in the practice of this invention.

Referring now to FIG. 1, this invention is employed to replace an existing endotracheal tube in an intubated patient with a new endotracheal tube. The endotracheal tube 10 is, as illustrated in FIG. 1 inserted through the mouth having at an external end, a connection piece 12 and at a lower end a tapered tip 14. Further, such a device has an inflatable annular cuff 16 which is coupled to a syringe connector 18 via tube 20. The obturator 22 (to be discussed in detail herein) is inserted into the endotracheal tube 20 with its tapered flexible tip 24 extending through the end 14. The obturator is slid through the tube 10 until a replacement mark on the tube 26 is aligned with the connection 12.

Figure 2:
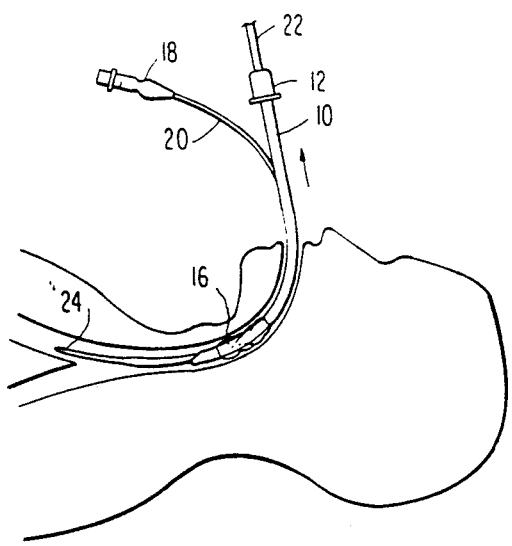
Figure 3:
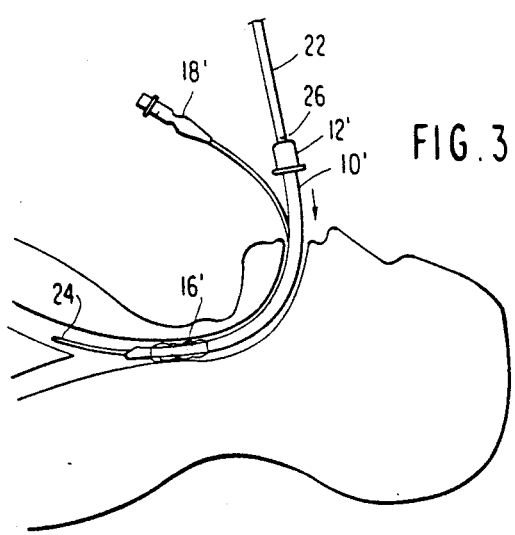

Referring next to FIG. 2 the cuff 16 is deflated by retracting the plunger on a syringe connected to the connector 18. The tube 10 is then slid upward in the direction of the arrow in FIG. 2 while the technician maintains the obturator 22 in place. Thus, as illustrated in the figure, the flexible tip 24 is maintained in the distal trachea such that the obturator does not move during withdrawal of the endotracheal tube. That is, the tube is slid upward utilizing the obturator 22 as a guide. When the tube 10 has been removed only the obturator is in the patient's air passage serving as a guide and at the same time maintaining the passage in an open condition. The original tube 10 can then be discarded and a new tube 10 inserted as illustrated in FIG. 3. This new endotracheal tube 10 slides over the obturator 22 until its connection end 12 is aligned with the replacement positioning mark 26. As illustrated in FIG. 3, the flexible tip 24 is maintained at the same position. That is, the replacement tube 10, slides over the obturator 22 which itself remains in position during this phase of the procedure.

Figure 4:
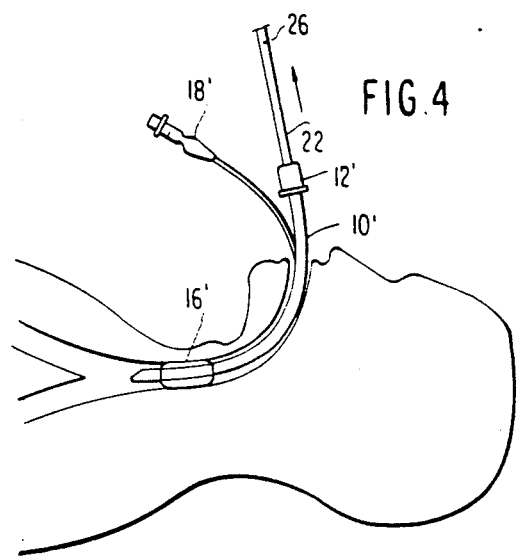

Then, as illustrated in FIG. 4, the obturator 22 is slid out of the new tube 10, as illustrated by the arrow in that figure then, utilizing a syringe coupled to the connector 18, the cuff 16 is inflated and its position verified in a routine manner.

As can be appreciated, during this procedure there is no need to relocate the endotracheal tube which is generally in excess of 7mm in inside diameter. Given the fact that the endotracheal tube while flexible, has a degree of stiffness, together with the variable anatomic complexity of the air passage to be travelled, having a guide with the proper degree of rigidity already in place materially enhances the speed, safety and reliability of the procedure.

Figure 5:
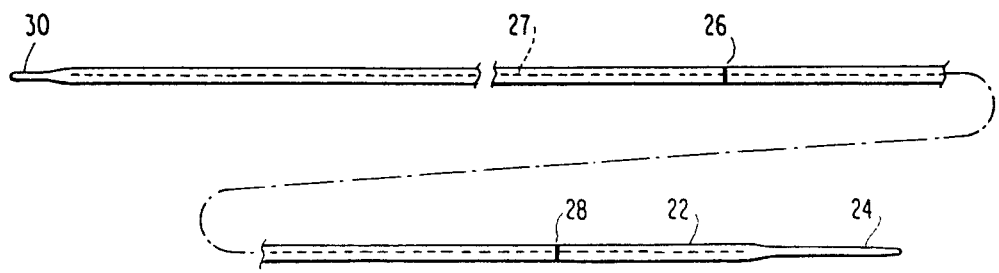
FIG. 5 is a schematic view of the obturator used in accordance with this invention.

Referring now to FIG. 5, the obturator of this invention is illustrated. The obturator is approximately 80cm in length having a diameter of approximately 19.0-French, approximately 0.63cm. The obturator is generally made utilizing a smooth elastomer or plastic sheath with a flexible metal core 27. In place of the flexible metal core a more rigid plastic or rubber material may be used. If desired, a siliconized coating may also be employed. The material should be radiopaque so as to allow for possible verification of positioning. In the case of a construction that does not use the metal core, a radiopaque material is mixed with the elastomer or plastic material.

The insertion or distal end 24 is made of the soft tapered sheath material to provide an atraumatic tip design. That is, as the tip 24 protrudes through the end of the endotracheal tube 14, as illustrated in FIG. 1, it may touch the wall of the carino or bronchus and therefore should be capable of deflection in an atraumatic manner.

The opposite or proximal end 30, has a radially modified gripping portion. That handle portion may also be a knurled or annular set of grooves around the body of the obturator 22 to provide the necessary gripping action for the practitioner. Portion 30 may have as shown a reduced portion to permit clamping or the like as a technique of maintaining the position of the obturator.

FIG. 5 illustrates two positioning marks. Mark 26 is used for endotracheal tube replacement while mark 28 is used for tracheostomy tube replacement. It will be appreciated that since the site of entry in a tracheostomy is different from that in an oro or naso-endotracheal procedure, mark 28 is placed closer to the distal insertion end 24 than mark 26.

The 80cm length is chosen to be approximately twice the length of a standard endotracheal tube. It is apparent, however, that this length can vary as a function of procedure. Moreover the external diameter of the obturator is chosen as a function of the tube into which it will be placed. The 19.0French diameter is chosen for use in replacement of tubes whose inner diameter is at least 7mm but no greater than 9mm. However, it is again apparent that the external diameter of the obturator 22 may vary as the internal diameter of the endotracheal tube also changes.

This invention is subject to other departures and modifications without varying from the essential scope thereof.

Having described my invention, I claim:

1. Apparatus for replacing a tracheal tube comprising:
   a elongated flexible obturator having a length sufficient to be inserted in one end of a tracheal tube and protrude through the distal end thereof with an uninserted length protruding from the proximal end, said obturator having a width to permit passage through said tracheal tube and maintain an opening in a patient's trachea following withdrawal of said tracheal tube, said obturator further comprising; a cover and a core, said cover made from an elastomer or plastic material, a flexible soft atraumatic tip at an insertion end defined by an elongated tapering solely of said cover and gripping means at an opposite end, and at least one positioning mark to provide a point of reference when one tracheal tube is replaced by another using said obturator as an in-vivo guide.

2. The apparatus of claim 1, wherein said obturator comprises two positioning marks at spaced locations, one positioning mark being reference for an endotracheal tube replacement and a second mark being a reference for a tracheostomy tube replacement.

3. The apparatus of claim 1, wherein said obturator comprises a radiopaque material.

4. The apparatus of claim 3, wherein said radiopaque material is flexible metal wire.

5. The apparatus of claim 1, wherein said obturator core is made from a metallic material.

* * * * *